United States Patent
Mariella, Jr. et al.

(10) Patent No.: US 7,090,979 B2
(45) Date of Patent: Aug. 15, 2006

(54) DERIVATIZED VERSIONS OF LIGASE ENZYMES FOR CONSTRUCTING DNA SEQUENCES

(75) Inventors: Raymond P. Mariella, Jr., Danville, CA (US); Allen T. Christian, Tracy, CA (US); James D. Tucker, Novi, MN (US); John M. Dzenitis, Livermore, CA (US); Alexandros P. Papavasiliou, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 241 days.

(21) Appl. No.: 10/718,856

(22) Filed: Nov. 21, 2003

(65) Prior Publication Data

US 2005/0059029 A1    Mar. 17, 2005

Related U.S. Application Data

(60) Provisional application No. 60/428,581, filed on Nov. 22, 2002.

(51) Int. Cl.
*C12Q 1/68* (2006.01)
*C12P 19/34* (2006.01)

(52) U.S. Cl. .................. 435/6; 435/91.5; 435/91.52

(58) Field of Classification Search .................. None
See application file for complete search history.

(56) References Cited

U.S. PATENT DOCUMENTS 5,580,759 A    12/1996    Yang et al.
5,652,107 A *  7/1997    Lizardi et al. ............... 435/6
5,942,609 A *  8/1999    Hunkapiller et al. ....... 536/25.3
6,110,668 A *  8/2000    Strizhov et al. ............ 435/6
6,372,497 B1   4/2002    Stemmer
6,375,903 B1   4/2002    Cerrina et al.
2002/0076805 A1* 6/2002  Virtanen ................ 435/287.1

FOREIGN PATENT DOCUMENTS

WO    WO 02/095073 A1    11/2002

OTHER PUBLICATIONS

Sgaramella V, et al. 1970. Studies on Polynucleotides C, a novel joining reaction catalyzed by the T4-Polynucleotide Ligase. PNAS. vol. 67, No. 3, pp. 1468-1475.*
Khorana, HG. 1979. Total Synthesis of a Gene. vol. 203, pp. 614-625.*
Gearing, DP. 1985. Chemical Synthesis of a mitochondrial gene designed for expression in the yeast nucleus. Biochemistry International. vol. 10, No. 6, pp. 907-915.*

* cited by examiner

*Primary Examiner*—Jeffrey Fredman
*Assistant Examiner*—Stephanie K. Mummert
(74) *Attorney, Agent, or Firm*—Eddie E. Scott; Alan H. Thompson

(57) ABSTRACT

A method of making very long, double-stranded synthetic poly-nucleotides. A multiplicity of short oligonucleotides is provided. The short oligonucleotides are sequentially hybridized to each other. Enzymatic ligation of the oligo-nucleotides provides a contiguous piece of PCR-ready DNA of predetermined sequence.

10 Claims, 1 Drawing Sheet

DERIVATIZED VERSIONS OF LIGASE ENZYMES FOR CONSTRUCTING DNA SEQUENCES

CROSS-REFERENCE TO RELATED APPLICATIONS

This application claims the benefit of U.S. Provisional Patent Application No. 60/428,581 filed Nov. 22, 2002 and titled "Derivatized Versions of Ligase Enzymes for Constructing DNA Sequences." U.S. Provisional Patent Application No. 60/428,581 filed Nov. 22, 2002 and titled "Derivatized Versions of Ligase Enzymes for Constructing DNA Sequences" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to constructing DNA sequences and more particularly to constructing DNA sequences using ligase enzymes.

2. State of Technology

U.S. Pat. No. 6,375,903 issued Apr. 23, 2002 to Francesco Cerrina et al. for a method and apparatus for synthesis of arrays of DNA probes provides the following background information, "The sequencing of deoxyribonucleic acid (DNA) is a fundamental tool of modern biology and is conventionally carried out in various ways, commonly by processes which separate DNA segments by electrophoresis. . . . One such alternative approach, utilizing an array of oligonucleotide probes synthesized by photolithographic techniques is described in Pease, et al., "Light-Generated Oligonucleotide Arrays for Rapid DNA Sequence Analysis," Proc. Natl. Acad. Sci. USA, Vol. 91, pp. 5022–5026, May 1994."

International Patent Application WO 02/095073 by Peter J. Belshaw et al. published Nov. 28, 2002 for a method for the synthesis of DNA sequences provides the following background information, "Using the techniques of recombinant DNA chemistry, it is now common for DNA sequences to be replicated and amplified from nature and for those sequences to then be disassembled into component parts which are then recombined or reassembled into new DNA sequences. While it is now both possible and common for short DNA sequences, referred to as oligonucleotides, to be directly synthesized from individual nucleosides, it has been thought to be generally impractical to directly construct large segments or assemblies of DNA sequences larger than about 400 base pairs. As a consequence, larger segments of DNA are generally constructed from component parts and segments which can be purchased, cloned or synthesized individually and then assembled into the DNA molecule desired."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a method of making very long, double-stranded synthetic poly-nucleotides by ligating strands of DNA using a complementary sequence as a template and a ligase. In one embodiment of the invention a multiplicity of short oligonucleotides are provided. The short oligonucleotides are sequentially hybridized to each other. Enzymatic ligation of the oligonucleotides provides a contiguous piece of PCR-ready DNA of predetermined sequence. In another embodiment of the invention a multiplicity of short single-stranded oligonucleotides are provided. The short single-stranded oligonucleotides are sequentially hybridized to each other. Enzymatic ligation of the oligonucleotides provides a contiguous piece of PCR-ready DNA of predetermined sequence. Another embodiment of the invention comprises making long, double-stranded synthetic poly-nucleotides by providing a multiplicity of short single-stranded oligonucleotides, sequentially hybridizing said short single-stranded oligonucleotides to each other, and enzymatic ligating said short single-stranded oligonucleotides to provide a contiguous piece of PCR-ready double stranded DNA of predetermined sequence.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
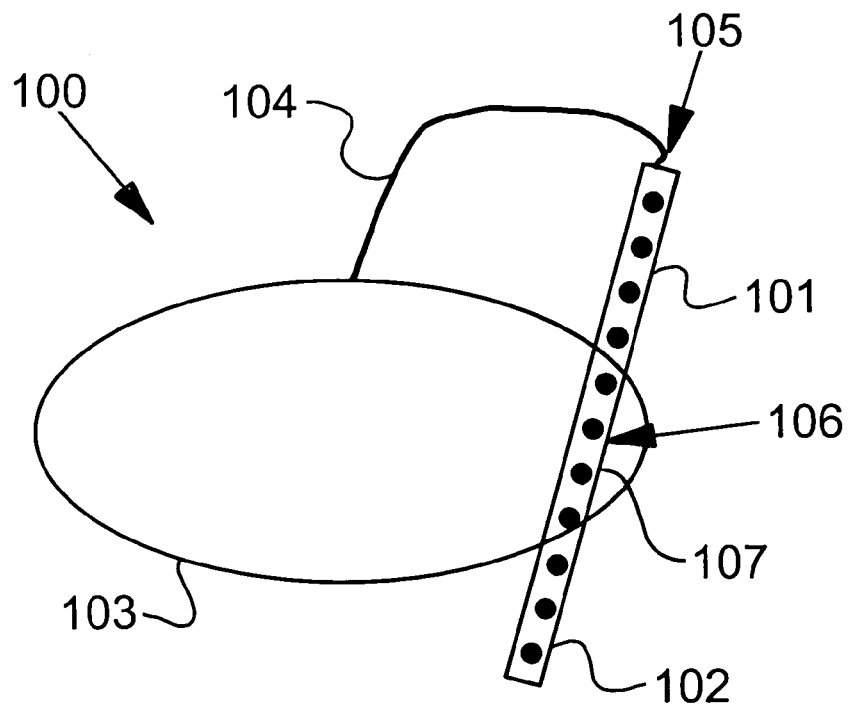
FIG. 1 is an illustration showing that the ligase or the linker or the ds-DNA may also be attached to a surface.

Referring now to the drawings, to the following detailed description, and to incorporated materials; detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Artificial gene synthesis is a widely used tool in molecular biology. Its utility is evidenced by, among other things, the gene synthesis services provided by more than a dozen companies worldwide. Uses include such common biological purposes as genes for transgenic studies, genetic engineering and mutagenesis, and uses as esoteric as encryption and DNA computing. The techniques for making synthetic genes are fundamentally understood; short oligonucleotides are made by phosphoramidite synthesis, and are then either joined together using DNA ligase, hybridized and extended using DNA polymerase, or created using various combinations of the two enzymatic approaches. The enzymatic processes themselves are relatively rapid and inexpensive; the factor that drives the cost and deliverable time of artificial genes is the need for phosphoramidite synthesis. A casual survey of gene synthesis service websites provides a cost per base of approximately $10.00 for genes longer than 2 kilobases; as the average gene is around 7000 bases, it is reasonable to expect to pay in the neighborhood of $70,000 to purchase an artificial gene. It is this cost, and the considerable delivery time, that has kept artificial genes from being as widely-used as they might otherwise be. DNA computing, for example, requires much more rapid turn-around; hours or days rather than weeks or months are necessary.

The two predominant factors in this price are labor and the price of the oligonucleotides. While both ligation and polymerase extension will work on oligos of a variety of lengths, 40 bases is the median length reported in the literature as starting substrates. Depending on the overlap necessary to assemble the oligos into a final product, a minimum of 350 oligos are required to make a 7000 base-pair gene. To synthesize the oligonucleotides required for this makes up an enormous fraction of the $70,000 estimated cost; the average market rate to buy these phosphoramidite-synthesized nucleotides is approximately $50,000. Clearly, a more cost-effective means of gene synthesis is called for, and preferably a synthesis method that permits more rapid delivery. The utility of synthetic long DNA and artificial genes is limited by the cost and time required to produce them. The primary cost factors involved are labor, the oligonucleotides that serve as building blocks for the final product, enzymes and sequencing verification.

Applicants have developed a process to make very long, double-stranded synthetic poly-nucleotides. This process consists of sequentially hybridizing short single-stranded oligonucleotides (oligos) to each other, followed by enzymatic ligation. This results in a contiguous piece of PCR-ready double stranded DNA of predetermined sequence that can be extended many thousands of base pairs.

Referring now to FIG. 1, one embodiment of the present invention is illustrated. The embodiment is a system designated generally by the reference numeral 100. The embodiment 100 comprises a method of making very long, double-stranded synthetic poly-nucleotides. A multiplicity of short oligonucleotides is provided. The short oligonucleotides are sequentially hybridized to each other. Enzymatic ligation of the nucleotides provides a contiguous piece of PCR-ready DNA of predetermined sequence.

The system 100 that includes means for ligating two single strands of DNA using a complementary sequence as a template and a ligase. Caches of the different possible DNA oligomers, such as tetramers or 8-mers, are synthesized by conventional phosphoramidite synthesis prior to the long poly-nucleotide synthesis, and kept in the synthesis device to be drawn upon as needed to create the desired molecule. This makes the long-strand nucleotide synthesis independent of in loco phosphoramidite syntheses. The process requires that several different components be brought to one place for the reaction to proceed. In one embodiment, Applicants use the ligase (enzyme) to take two single-stranded tetramers and produce a single-stranded 8-mer via hybridization to a complementary 8-mer and subsequent action of a ligase. Applicants bring together the complementary 8-mer, both tetramers, and the ligase.

The method 100 includes the steps of ligating two single strands of DNA using a complementary sequence as a template and a ligase. As illustrated in FIG. 1, ds-DNA 102 and ds-DNA 103 are separated by an active site 106 for hybridization and ligation. A template 107 is provided at the site.

There are kinetic, thermodynamic, and logistical challenges to this process. Applicants address all three of these challenges by chemically coupling the ligase to the complementary DNA sequence, and, in one embodiment, coupling the complementary DNA sequence either to a fixed surface or, for the purpose of manipulations, to the surface of a bead. In this manner, the overall DNA ligation process can be made more efficient.

A ligase 103 or the linker 104 or the ds-DNA 102 and 103 are attached to a surface. The system 100 makes very long, double-stranded synthetic poly-nucleotides. The system 100 comprises sequentially hybridizing short single-stranded oligonucleotides (oligos) to each other, followed by enzymatic ligation. This results in a contiguous piece of PCR-ready double stranded DNA of predetermined sequence that can be extended many thousands of base pairs.

DNA molecules can be synthesized using array technology that is known in the art. For example, U.S. Pat. No. 6,238,868, incorporated herein by reference, provides the following information, "microchip device is an electronically controlled microelectrode array. See, PCT application WO96/01836, the disclosure of which is hereby incorporated by reference. In contrast to the passive hybridization environment of most other microchip devices, the electronic microchip devices (or active microarray devices) of the present invention offer the ability to actively transport or electronically address nucleic acids to discrete locations on the surface of the microelectrode array, and to bind the addressed nucleic acid at those locations to either the surface of the microchip at specified locations."

The system 100 allows the individual scientist to maintain all of the necessary reagents for DNA synthesis in storage. When a specific long DNA sequence is desired, they are combined and assembled, as directed by the output of a computer program. This process allows rapid and inexpensive gene synthesis to be a widely available tool. These oligos can be synthesized by any of the many platforms extant; the sole requirements being that they are amenable to be copied and extended by DNA polymerases.

In one embodiment the design details include chemical modifications to the complementary sequence so that the ligase does not permanently attach itself to the DNA from solution. When Applicants are ligating two single-stranded pieces of DNA via their hybridization to a complementary template which has been tethered to a ligase enzyme, then hundreds or thousands of such ligations can be performed before the enzyme becomes degraded. If Applicants are repeatedly adding either single- or double-stranded DNA to a growing piece of double-stranded DNA which is tethered to the ligase enzyme, then hundreds or thousands of such ligations can be performed before the enzyme becomes degraded.

The present invention increases the ease of ligating two single strands of DNA, using a complementary sequence as a template and a ligase (enzyme) to perform the chemistry. Under the appropriate pH conditions, for which the ligase is active, it can join two strands of DNA together. Embodiments of the invention include ligase joining two strands of DNA (both "blunt-end and "sticky-end" ligations). In one embodiment, the ligase joins two single-strands of DNA, using a second complementary strand as a template.

The process utilizes repeated ligations which continues until the consumption of the ligase enzyme is exhausted. If the enzyme is chemically linked to its template and also either directly linked to a surface or its template is linked to a surface, then the ligase can be re-used numerous times in a repeated, serial process of adding one strand of DNA at a time to a growing strand.

The process 100 can be summarized as a method of making very long, double-stranded synthetic poly-nucleotides. The method 100 comprising the steps of providing a multiplicity of short single-stranded oligonucleotides, sequentially hybridizing the short single-stranded oligonucleotides to each other, and enzymatic ligating the short single-stranded oligonucleotides to provide a contiguous piece of PCR-ready double stranded DNA of predetermined sequence. One embodiment of the method 100 comprises ligating two single strands of DNA using a complementary sequence as a template and a ligase. One embodiment of the method 100 utilitzes a complementary sequence as a template. Another embodiment of the method 100 utilitzes a complementary sequence as a template and a ligase. Another embodiment of the method 100 utilizes a ligase.

In one embodiment of the method 100 the step of enzymatic ligating utilizes a linker. In another embodiment of the method 100 the step of enzymatic ligating utilizes ds-DNA. In another embodiment of the method 100 the step of enzymatic ligating utilizes a surface with a template at the surface. In another embodiment of the method 100 the step of ligating utilizes a surface with a linker at the surface. In another embodiment of the method 100 the step of enzymatic ligating utilizes a surface with a ds-DNA at the surface. In another embodiment of the method 100 the step of enzymatic ligating utilizes hybridization to a complementary template which has been tethered to a ligase enzyme. In another embodiment of the method 100 the step of enzymatic ligating utilizes ligase joining two strands of DNA. In another embodiment of the method 100 the step of enzymatic ligating utilizes blunt-end ligase joining two strands of DNA. In another embodiment of the method 100 the step of enzymatic ligating utilizes sticky-end ligase joining two strands of DNA. In another embodiment of the method 100 the step of enzymatic ligating utilizes ligase wherein the ligase joins two single-strands of DNA. In another embodiment of the method 100 the step of enzymatic ligating utilizes ligase the ligase joins two single-strands of DNA using a second complementary strand. In another embodiment of the method 100 the step of enzymatic ligating utilizes ligase wherein said ligase joins two single-strands of DNA using a second complementary strand as a template.

One embodiment of the method of constructing poly-nucleotides 100 includes repeatedly adding single-stranded DNA to a growing piece of double-stranded DNA which is tethered to the ligase enzyme. Another embodiment of the method of constructing poly-nucleotides 100 includes repeatedly adding double-stranded DNA to a growing piece of double-stranded DNA which is tethered to the ligase enzyme. Another embodiment of the method of constructing poly-nucleotides 100 includes repeatedly adding either single-stranded DNA or double-stranded DNA to a growing piece of double-stranded DNA. Another embodiment of the method of constructing poly-nucleotides 100 includes repeatedly adding either single-stranded DNA or double-stranded DNA to a growing piece of double-stranded DNA that are combined and assembled as directed by the output of a computer program.

Figure 2:
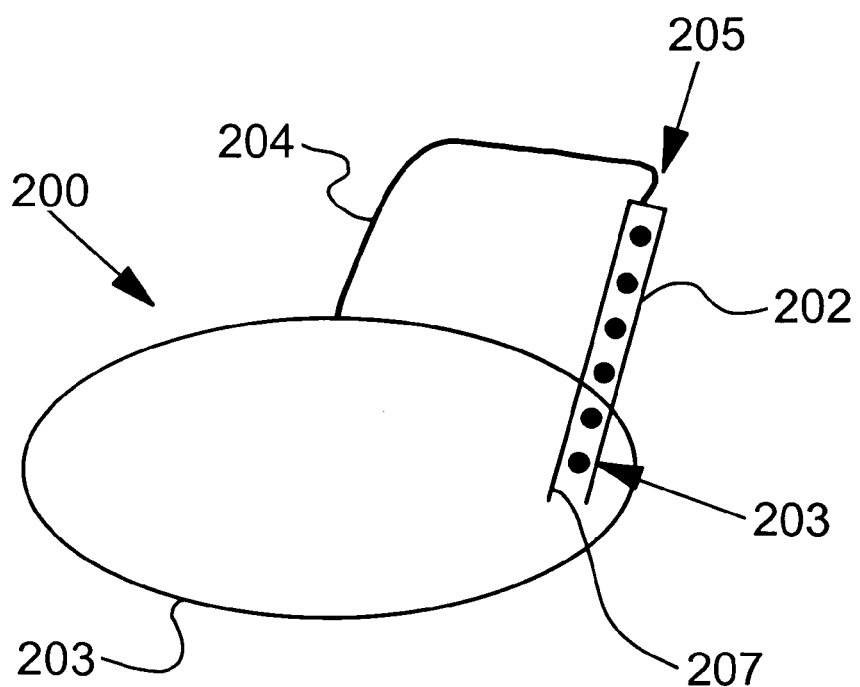
FIG. 2 is another illustration showing that the ligase or the linker or the ds-DNA may also be attached to a surface.

Referring now to FIG. 2, an illustration shows another embodiment of a system wherein the ligase or the linker or the ds-DNA are attached to a surface. The embodiment is designated generally by the reference numeral 200. The embodiment 200 comprises a method of making very long, double-stranded synthetic poly-nucleotides. A multiplicity of short oligonucleotides is provided. The short oligonucleotides are sequentially hybridized to each other. Enzymatic ligation of the oligonucleotides provides a contiguous piece of PCR-ready DNA of predetermined sequence.

The system 200 that includes means for ligating two single strands of DNA using a complementary sequence as a template and a ligase. Caches of the different possible DNA oligomers, such as tetramers or 8-mers, are synthesized by conventional phosphoramidite synthesis prior to the long poly-nucleotide synthesis, and kept in the synthesis device to be drawn upon as needed to create the desired molecule. This makes the long-strand nucleotide synthesis independent of in loco phosphoramidite syntheses. The process requires that several different components be brought to one place for the reaction to proceed. In one embodiment, Applicants use the ligase (enzyme) to take two single-stranded tetramers and produce a single-stranded 8-mer via hybridization to a complementary 8-mer and subsequent action of a ligase. Applicants bring together the complementary 8-mer, both tetramers, and the ligase.

The method 200 includes the steps of ligating strands of DNA using a template 207 and a ligase 203. The complementary DNA sequence is either to a fixed surface or, for the purpose of manipulations, to the surface of a bead. In this manner, the overall DNA ligation process can be made more efficient. The ligase 203 with a linker 204 or the ds-DNA 202 is attached to a surface. The ligase 203 joins strands of DNA with "sticky-end 203" ligations. The system 200 makes very long, double-stranded synthetic poly-nucleotides. The system 200 comprises sequentially hybridizing short single-stranded oligonucleotides (oligos) to each other, followed by enzymatic ligation. This results in a contiguous piece of PCR-ready double stranded DNA of predetermined sequence that can be extended many thousands of base pairs.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of constructing poly-nucleotides, comprising the steps of:
  a) providing a mixture comprising a nucleic acid template chemically coupled to a protein ligase and single stranded DNAs complementary to the template, for ligation,
  b) ligating strands of DNA using a protein ligase and a complementary sequence as a template, wherein said step of ligating utilizes hybridization to a complementary template which has been chemically coupled to a protein ligase enzyme.

2. The method of constructing polynucleotides of claim 1 including repeatedly adding single-stranded DNA to a growing piece of double-stranded DNA which is tethered to a protein ligase enzyme.

3. The method of constructing polynucleotides of claim 1 including repeatedly adding double-stranded DNA to a growing piece of double-stranded DNA which is tethered to a protein ligase enzyme.

4. A method of constructing very long, double-stranded synthetic poly-nucleotides comprising the steps of:
   a) providing a mixture comprising a nucleic acid template chemically coupled to a protein ligase and single stranded DNAs complementary to the template, for ligation,
   b) providing a multiplicity of oligonucleotides,
   c) sequentially hybridizing said oligonucleotides to each other, and
   d) enzymatic ligating said oligonucleotides to provide a contiguous piece of DNA of predetermined sequence, wherein said step of enzymatic ligating utilizes hybridization to a complementary template which has been chemically coupled to a protein ligase enzyme.

5. The method of constructing polynucleotides of claim 4 including repeatedly adding single-stranded DNA to a growing piece of double-stranded DNA which is tethered to a protein ligase enzyme.

6. The method of constructing polynucleotides of claim 4 including repeatedly adding double-stranded DNA to a growing piece of double-stranded DNA which is tethered to a protein ligase enzyme.

7. The method of constructing polynucleotides of claim 1 including repeatedly adding either single-stranded DNA or double-stranded DNA to a growing piece of double-stranded DNA which is tethered to a protein ligase enzyme.

8. A method of constructing very long, double-stranded synthetic polynucleotides comprising the steps of:
   a) providing a mixture comprising a nucleic acid template chemically coupled to a protein ligase and single stranded DNAs complementary to the template, for ligation,
   b) providing a multiplicity of short single-stranded oligonucleotides,
   c) sequentially hybridizing said short single stranded oligonucleotides to each other, and
   d) enzymatic ligating said short single-stranded oligonucleotides to provide a contiguous piece of double stranded DNA of predetermined sequence, wherein said step of ligating utilizes hybridization to a complementary template which has been chemically coupled to a protein ligase enzyme.

9. The method of constructing polynucleotides of claim 8 including repeatedly adding single-stranded DNA to a growing piece of double-stranded DNA which is tethered to a protein ligase enzyme.

10. The method of constructing polynucleotides of claim 8 including repeatedly adding double-stranded DNA to a growing piece of double-stranded DNA which is tethered to a protein ligase enzyme.

* * * * *